United States Patent [19]

Sayama et al.

[11] Patent Number: 5,062,127
[45] Date of Patent: Oct. 29, 1991

[54] METALS ASSAY APPARATUS AND METHOD

[75] Inventors: Yasumasa Sayama, Saitama; Koichi Nomura, Tokyo; Morihiko Iwasaki, Kagawa, all of Japan

[73] Assignee: Mitsubishi Metal Corporation, Tokyo, Japan

[21] Appl. No.: 524,045

[22] Filed: May 16, 1990

[30] Foreign Application Priority Data

May 16, 1989 [JP] Japan .................................. 1-122632

[51] Int. Cl.$^5$ ........................................... G01N 23/22
[52] U.S. Cl. ...................................... 378/45; 378/48; 378/99; 378/207
[58] Field of Search ...................... 378/98, 83, 50, 49, 378/47, 44–48, 207, 99, 88

[56] References Cited

U.S. PATENT DOCUMENTS

| | | | |
|---|---|---|---|
| 3,764,805 | 10/1973 | Alley | 378/48 |
| 3,983,397 | 9/1976 | Albert | 378/93 |
| 4,045,676 | 8/1977 | Rolle | 378/48 |
| 4,121,098 | 10/1978 | Jagoutz et al. | 378/49 |
| 4,359,638 | 11/1982 | Allport | 378/50 |
| 4,370,751 | 1/1983 | Pink et al. | 378/47 |
| 4,426,717 | 1/1984 | Schwenke et al. | 378/45 |
| 4,429,409 | 1/1984 | Berry et al. | 378/48 |
| 4,510,573 | 4/1985 | Boyce et al. | 378/48 |
| 4,577,338 | 3/1986 | Takahashi et al. | 378/48 |
| 4,796,284 | 1/1989 | Jenkins | 378/49 |
| 4,885,465 | 12/1989 | Nagatsuka et al. | 378/45 |

Primary Examiner—Edward P. Westin
Assistant Examiner—Kim-Kwok Chu
Attorney, Agent, or Firm—Oblon, Spivak, McClelland, Maier & Neustadt

[57] ABSTRACT

The present invention discloses an Fluorescence X-ray spectrometry method and device for determining the type and quantity of metals elements in metal and metal alloy samples, particularly precious metal and precious metal alloy samples. The invention provides a method and an apparatus in which an object to be analyzed is positioned so that an X-ray beam that will be generated will coincide with a measurement point on the surface of the object where it is desired that the analysis be carried out. The measurement point is exposed to an X-ray beam having a diameter of 0.1 to 5 mm, causing fluorescence X-ray radiation to be generated which is sampled. Spectral analysis of the captured fluorescence X-ray radiation is then carried out wherein the intensity of selected peaks corresponding to target elements is determined, whereby the relative composition of selected elements can be calculated, thus providing selective quantitative analysis for target elements at the measurement point. The relative composition can be calculated by performing a computer analysis of the spectrum of the captured fluorescence X-ray radiation in which a fundamental parametric method is applied to the intensity values for peaks corresponding to each target element.

12 Claims, 15 Drawing Sheets

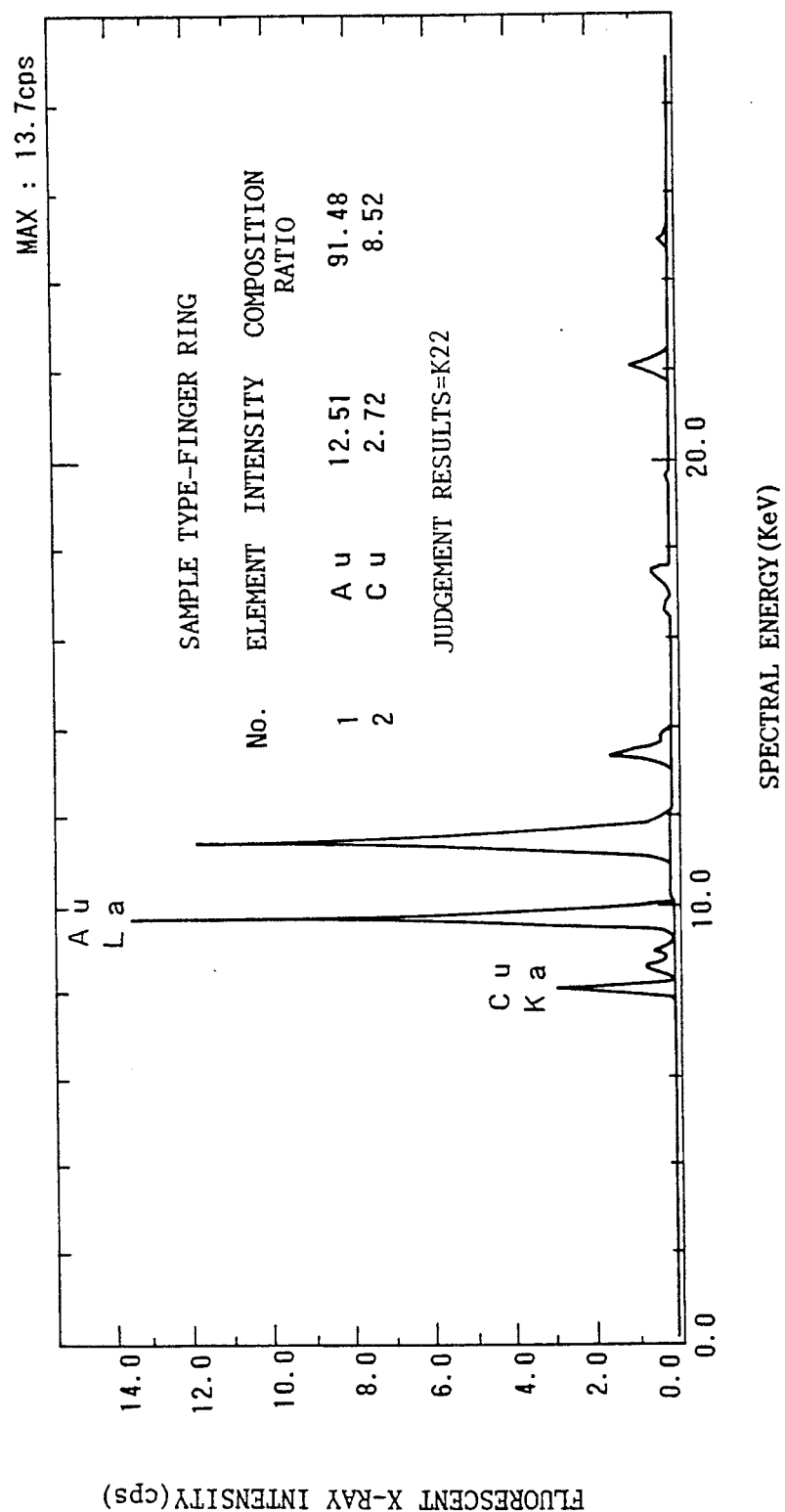

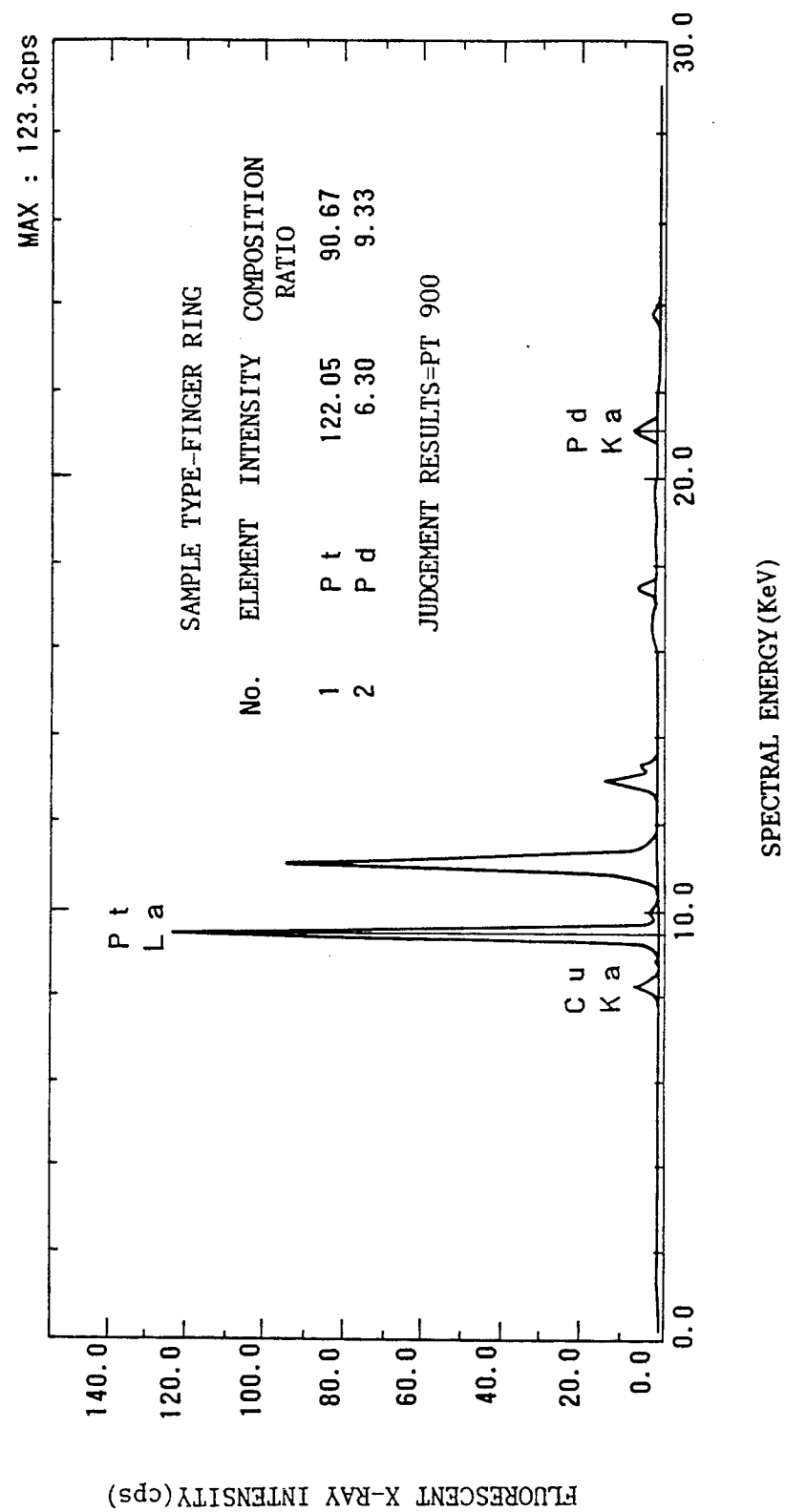

METALS ASSAY APPARATUS AND METHOD

BACKGROUND OF THE INVENTION

1. Field of the Invention

The present invention pertains to methods and devices for determining the metal content of metallic materials, alloys, etc.. In particular, the present invention is concerned with methods and devices used to appraise the precious metal content of jewelry and other articles fabricated from precious metals.

2. Prior Art

In recent years, there has been increasing demand for a means whereby for the sake of improving the efficiency and verity of transactions, dealers in jewelry, precious metals and the like can easily, accurately and at their place of business appraise the metal content and composition of articles fabricated from precious metals. Conventionally, the value of such articles has been appraised using the touchstone method, specific gravity measurement, fire assay method, atomic absorption spectrometry, inductively coupled plasma spectrometry (ICP) and the like. Unfortunately, as will be described below, various problems are associated with each of these methods which render them impractical for accurate appraisal performed at the place of business where transactions in such articles are carried out.

In the case of the touchstone method, a portion of the article to be tested is rubbed against a black quartz test stone whereby a streak is obtained on the test stone which is then treated with acid by which means the composition of the test article can be determined. This test, however, requires a great deal of skill and experience, and furthermore, tends to mar the article being tested. Additionally, this test is not applicable to some white golds (gold - palladium alloys) and platinum alloys which are significantly hard, nor to significantly soft materials such as fine gold or alloys containing more than 92% gold.

Specific gravity determination is an easily performed method in which the weight of the article to be tested is determined while suspended in water. This method, however, can not be used to determine the composition of unknown samples.

The fire assay method, atomic absorption spectrometry, and inductively coupled plasma spectrometry are destructive methods and can therefore not be used on articles for sale.

In view of the above described shortcomings of conventional precious metal appraisal methods, the inventors of the present invention have studied a nondestructive Fluorescence X-ray spectrometry method. In this method, an assay sample is exposed to X-ray radiation, whereby fluorescence X-ray radiation is generated upon which spectral analysis is carried out whereby quantitative analysis of each elemental component can be accomplished simultaneously.

Conventional equipment marketed for carrying out fluorescence X-ray spectrometry, however, requires an assay sample having a homogeneous, and flat and even surface. For this reason, in addition to the difficulty of choosing the best point on the sample to which the analysis is to be directed, because the X-ray beam is of a relatively large diameter (ordinarily 20 mm or greater), small specimens having a complex structure, or specimens made up of a number of different alloys cannot be reliable assayed with such devices. Furthermore, conventional equipment marketed for carrying out fluorescence X-ray spectrometry is quite large and expensive. Thus, not only is a considerable capital investment required, but installation of such a devices consumes a great deal of space when installed in a store or other business cite. Additionally, operation of such a device requires quite specialized knowledge.

SUMMARY OF THE INVENTION

In consideration of the above, an object of the present invention is to provide an apparatus and method whereby assay of the metal content of articles fabricated from precious metals can reliably, accurately, and rapidly carried out, and wherein the required equipment is relatively inexpensive as well as of a compact size, and operation thereof can easily be accomplished by someone without extensive training Furthermore, the apparatus and method should be applicable even to small articles having a complex structure.

In order to achieve such an object, the present invention provides a metals assay method in which an object to be analyzed is positioned so that an X-ray beam that will be generated will coincide with a measurement point on the surface of the object where it is desired that the analysis be carried out. The sample having been thus positioned, the measurement point is exposed to an X-ray beam having a diameter of 0.1 to 5 mm, at which point fluorescence X-ray radiation is generated which is then sampled. Spectral analysis of the captured fluorescence X-ray radiation is then carried out wherein the intensity of selected peaks corresponding to target elements is determined, whereby the relative composition of selected elements can be calculated, thus providing selective quantitative analysis for target elements at the measurement point. The relative composition can be calculated by performing computer analysis of the spectrum of the captured fluorescence X-ray radiation in which a fundamental parametric method is applied to the intensity values for peaks corresponding to each target element.

Concerning the above mentioned fundamental parametric method, one approach is to apply the method to the peaks in the spectrum corresponding to a series of target elements, whereby from the intensity of the peaks of this series of target elements, a primary composition ratio is calculated for each target element. After the primary composition ratios have been thus calculated, for those target elements whose primary composition ratios are judged to have exceeded a predetermined target value, the fundamental parametric method is again applied to only those elements, whereby final primary composition ratios are determined for the selected target elements.

Another approach to application of the above mentioned fundamental parametric method is to determine the energy value corresponding to each peak in the obtained spectrum, after which the calculated energy values are compared with predetermined registered element energy values stored in the computer, whereby it is determined which of the peaks in the spectrum correspond with registered element energy values stored in the computer. Those peaks that correspond to registered element energy values stored in the computer are selected as target element peaks, after which the fundamental parametric method is applied to the selected target element peaks, whereby final primary composition ratios are determined for the selected target elements.

Additionally, by comparing the calculated target element composition ratios with predetermined precious metal alloy composition ratios stored in the computer, it is possible to determine the type of precious metal alloy for a sample article.

The metals assay apparatus of the present invention includes a movable stage, the position of which is adjustable in three dimensions on which an object to be analyzed can be supported, and an X-Y drive mechanism whereby the position of the movable stage can be adjusted in a plane parallel to the surface of the sample object at the point where it is desired to carry out the assay. Further included is a monitor whereby the relative position of the sample supported on the movable stage and the point at which the X-ray beam will be directed is displayed. A Z-axis position sensor is provided whereby the position of the sample relative to the Z-axis can be detected, the Z-axis being perpendicular to the surface of the sample object at the point where it is desired to carry out the assay. By means of a Z-axis position adjustment mechanism, based on the output signal of the Z-axis position sensor, the position of the movable stage along the Z-axis, that is, perpendicular to the surface of the sample object at the point where it is desired to carry out the assay, can be adjusted. An X-ray generator is provided including a collimator, whereby the area of the sample exposed to the X-ray beam can be adjustably limited to a diameter of 0.1 to 5 mm. A semiconductor detector is provided, by which means fluorescence X-ray radiation generated at the section of the sample exposed to the X-ray beam can be sampled. A computer along with a suitable computer output device is provided, whereby based on the sampled fluorescence X-ray radiation generated at the section of the sample exposed to the X-ray beam, composition ratios of target elements can be calculated.

Because the method and apparatus as described above are nondestructive, jewelry, coins and the like can be appraised as to their precious metal content without inflicting damage to their surfaces, or otherwise adversely affecting their value. Quantitative determinations for a number of precious metal elements can simultaneously carried out in a short length of time, by a process that is totally automated other than fixing the sample on the movable stage and selecting the spot to be analyzed.

By providing an adjustable collimator for the X-ray generator, by which means the section of the sample exposed to the X-ray beam can be limited to as small as a diameter of 0.1 mm, it is possible to analyze with high resolution quite small samples having a complicated shape and structure. In the case of samples having a large, flat and even surface, the diameter of the section of the sample exposed to the X-ray beam can be at the maximum diameter of 5 mm, whereby both the speed and the accuracy of the assay can be improved.

The present invention provides separate mechanisms for positioning the sample in the X-Y plane, that is, in the plane parallel to the surface of the sample at the point where it is desirable to carry out the assay, and for positioning the sample along the Z-axis, that is, perpendicular to the X-Y axis. Positioning in the X-Y plane is conducted by the operator using a monitor whereby the position of point to be measured relative to the point where the X-ray beam will be directed can be observed. Thus, since the position in the X-Y plane is selected manually by the operator, the assay can be directed towards any point on the surface of the sample. In this way, for composite samples fabricated from two or more different components, the metal composition of any component or portion of the sample can be determined. In the case of adjustment along the Z-axis, since depth is not readily observable on the monitor, the adjustment is carried out automatically by the Z-axis position adjustment mechanism based on the output signal from the Z-axis position sensor, whereby the position of the sample along the Z-axis can automatically be optimized to provide the most accurate assay.

Using the above described fundamental parametric method, calibration curves, standard samples and the like are unnecessary. Thus, determinations of the composition of unknown samples can reliably and easily be carried out. Further, by applying the fundamental parametric method to the peaks in the spectrum corresponding to target elements, whereby a primary composition ratio is calculated for each target element from the intensity of the peaks of the target elements, final primary composition ratios can be determined for target elements whose primary composition ratios are judged to have exceeded a predetermined target value. In this way, it becomes possible to rapidly assay a sample, determining composition ratios for only those components that are essential or sought after, while eliminating calculations for minor constituents, impurities, and the like.

Furthermore, when the method of the present invention is used in which the composition ratios are determined by calculating the energy value corresponding to each peak in the obtained spectrum, and then comparing the calculated energy values with predetermined energy values stored in the computer corresponding to know metal elements, by excluding those energy values that can easily be mistaken for target elements from the stored standard values, it becomes possible to eliminate mistaken identification of metal elements.

Moreover, while conventional precious metal appraisal methods are largely manual, with the method and apparatus of the present invention, appraisal of the content and composition of materials fabricated from precious metals can be nearly totally automated.

BRIEF DESCRIPTION OF THE DRAWINGS

FIGS. 8 through 16 are graphs showing spectra obtained in an experimental example using the metals assay apparatus of the present invention.

DETAILED DESCRIPTION OF THE PREFERRED EMBODIMENTS

In the following sections, the preferred embodiments of the present invention will be described with reference to the drawings.

Figure 1:
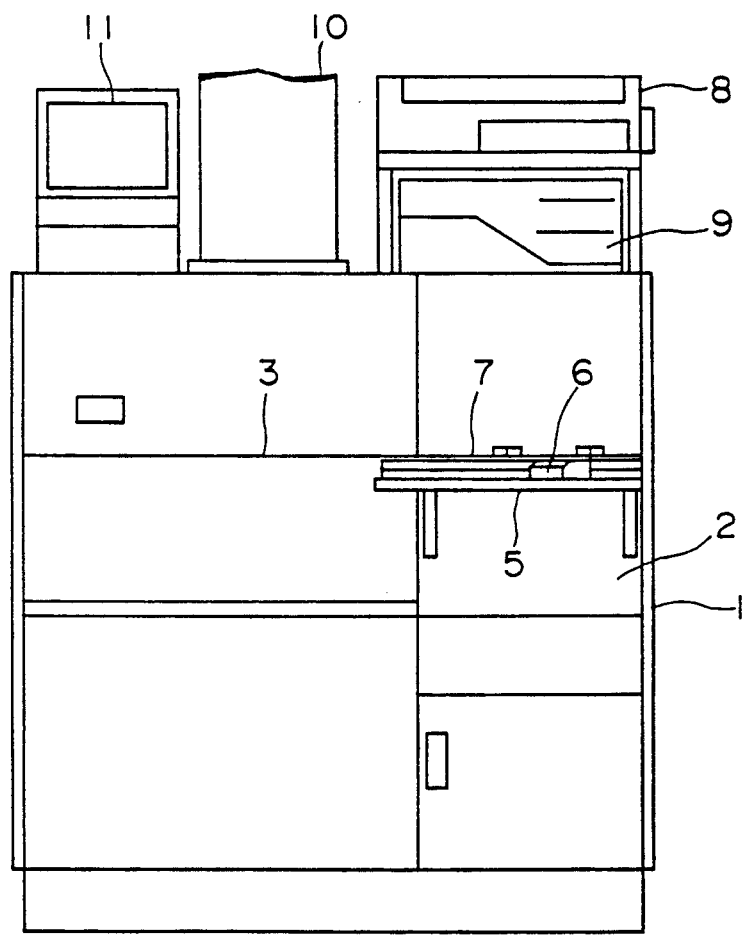
FIG. 1 is a front view showing the external structure to the metals assay apparatus of the present invention.
Figure 2:
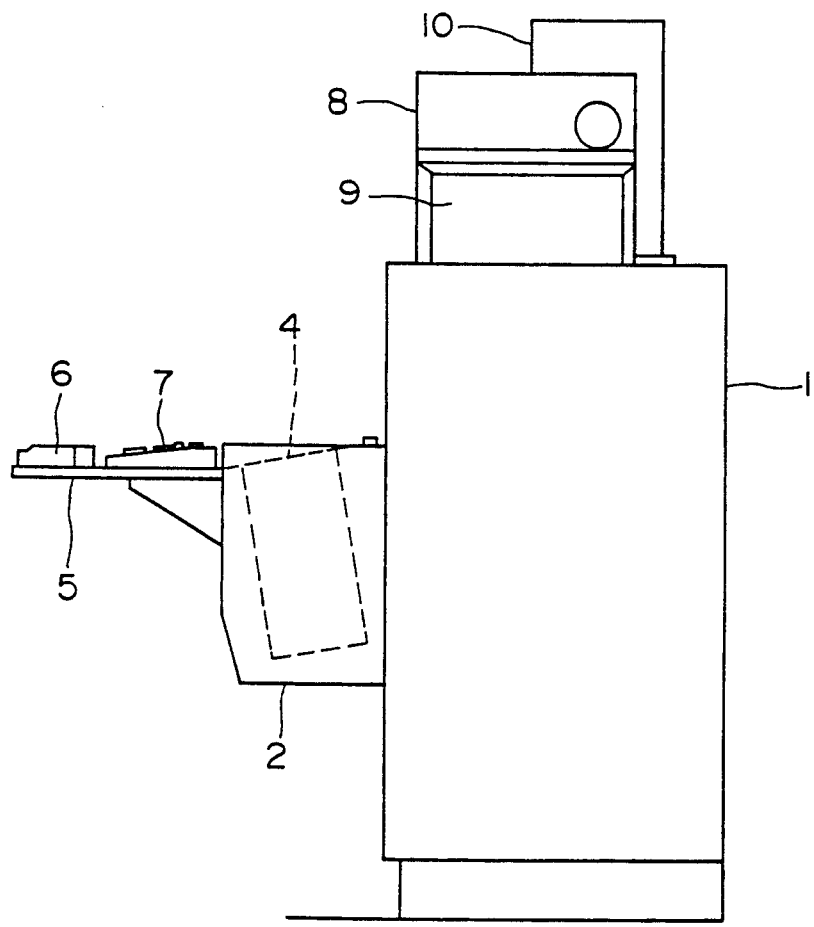
FIG. 2 is a right side view showing the external structure of the metals assay apparatus of the present invention.
Figure 3:
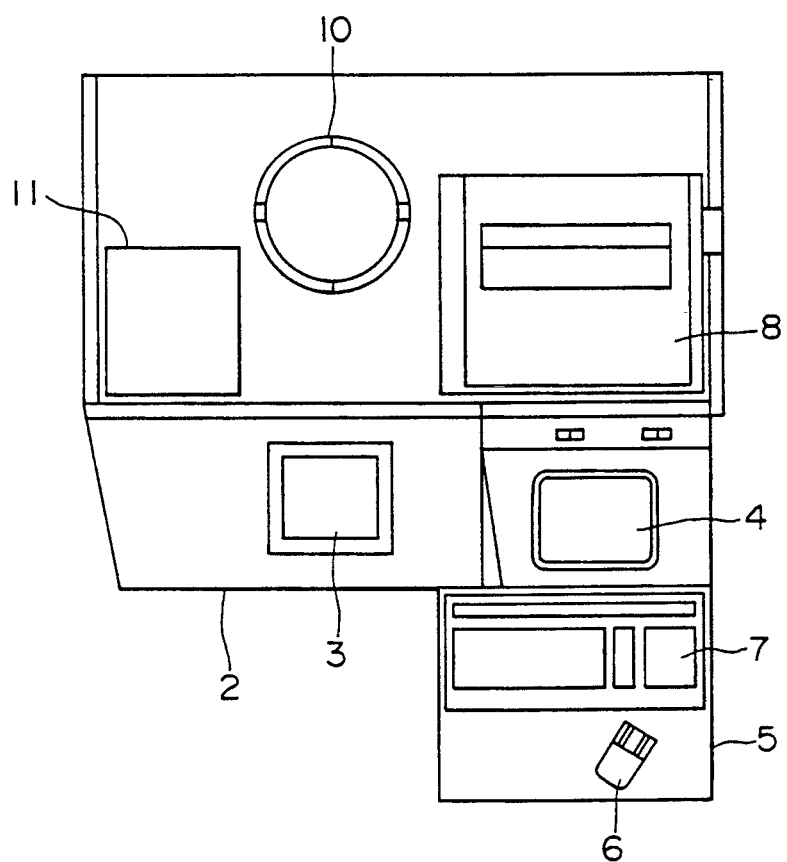
FIG. 3 is a plan view showing the external structure of the metals assay apparatus of the present invention.

In FIGS. 1 through 3, different aspects of the external appearance of the metals assay apparatus of the present invention are shown. As can be seen in the drawings, the main frame 1 of the apparatus is essentially box shaped. As seen best in FIGS. 2 and 3, a shelf 2 extends from the front apparatus of the main frame 1. At the left side of the shelf 2, a sample portal 3 is provided, while at the right side, a display screen 4 is provided. At the right front aspect of shelf 2, a retractable desk top 5 is provided, where a mouse 6 and keyboard 7 for data input and operation parameter selection may be situated during use. A printer 8 and computer 9 are located on the right side of the top of main frame 1. At the midportion of the top of main frame 1, a semiconductor detector 10 is located, while at the left portion, a sample position verification monitor 11 is provided.

Figure 4:
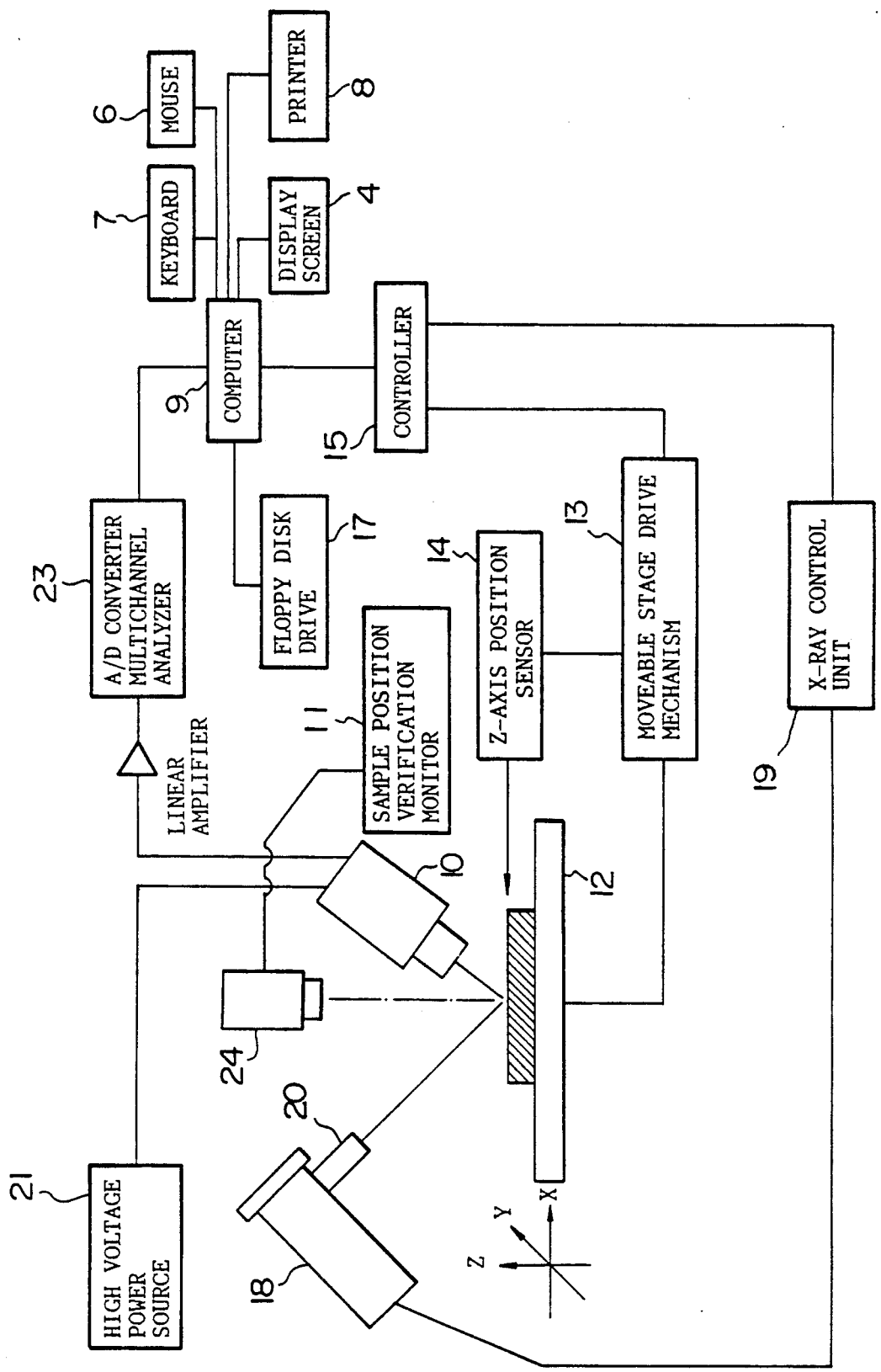
FIG. 4 is a block diagram of the metals assay apparatus pictured in FIGS. 1 through 3.

Referring to FIG. 4, the internal components of the metals assay apparatus of the present invention will be described. The sample to be assayed is placed on movable stage 12 which is provided in a horizontal orientation. By virtue of movable stage drive mechanism 13, which is in turn made up of an X-Y planar drive mechanism and a Z-axis linear drive mechanism, the position of movable stage 12 is adjustable in three dimensions. At one end of movable stage 12, an energy calibration reference sample (not shown in the drawings) is provided.

When a sample to be assayed is mounted on the upper surface of stage 12, the sample is mounted so that a flat surface of the sample faces upward and is aligned horizontally, using a mounting jig (not shown in the drawings). In the case where the sample consists of a finger ring, the ring is supported in a suitable mounting jig so as to secure the ring in a vertical orientation. Various mounting jigs are provided, whereby a sample of nearly any physical configuration can be easily mounted in an appropriate orientation, without inflicting any damage to the surface of the sample.

A Z-axis position sensor 14 is provided in close proximity to the movable stage 12, connected with the above mentioned movable stage drive mechanism 13. This Z-axis position sensor 14 can consist of, for example, an optical sensor and light source mounted in proximity to the movable stage 12 so that based on a beam of light from the light source being interrupted or reflected by the selected assay spot on the sample, the Z-axis position can be judged, on which basis a variable signal is supplied from the Z-axis position sensor 14 to the Z-axis linear drive mechanism component of the movable stage drive mechanism 13 via computer 9, thereby controlling the Z-axis linear drive mechanism to appropriately adjust the Z-axis position.

In ordinary operation, the movable stage 12 starts at its lowermost position. Then, based on a signal supplied from computer 9, the Z-axis linear drive mechanism component of movable stage drive mechanism 13 causes the movable stage 12 to move upward until, based on a signal from the above described Z-axis position sensor 14, the assay spot on the surface of the sample is judged to be a predetermined distance along the Z-axis from the above mentioned semiconductor detector 10, at which time the upward movement of movable stage 12 is automatically stopped. The reverse process in which the movable stage 12 normally rests in its uppermost position, then moves downward into position after a sample is mounted is also acceptable.

The X-Y planar drive mechanism component of movable stage drive mechanism 13 is connected with computer 9 via controller 15. Additionally connected with computer 9 are the above mentioned mouse 6, keyboard 7, and a floppy disk drive 17 as input devices, and the above mentioned display screen 4 and printer 8 as output devices.

An X-ray head 18 is provided above and to the side of movable stage 12 so that the X-ray beam generated by the X-ray tube housed therein forms approximately a 45° angle with the upper surface of movable stage 12 after passing through collimator 20 which is mounted on a side of X-ray head 18. Power for the X-ray tube housed in X-ray head 18 along with various operating parameters are supplied from an X-ray control unit 19 which is connected with computer 9 via controller 15, whereby the power and various operating parameters supplied to X-ray head 18 can be controlled based on control signals supplied from controller 15, which are in turn controlled based on signals from computer 9.

For the X-ray tube housed within X-ray head 18, a point focussing type X-ray tube may be used. The above mentioned collimator 20 includes a plurality of collimator elements (not shown in the drawings) of varying apertures, one of which is placed in the X-ray focal path through the action of a collimator selector mechanism (not shown), based on signals supplied from computer 9 via controller 15 and X-ray control unit 19. Through the above described collimator 20, the diameter of the spot on the sample exposed to X-ray radiation can be incrementally varied from 0.1 to 5 mm. At diameters less than 0.1 mm, the intensity of the fluorescence X-rays generated at the exposed spot is generally too small to measure over a suitably short measurement interval, and additionally, accuracy of the measured intensity suffers. Diameters greater than 5 mm for the exposed spot are seldom required for most articles that will be assayed using the apparatus of the present invention.

The previously mentioned semiconductor detector 10 located above movable stage 12 can be made from Si, Si(Li), Ge, Ge(Li), $HgI_2$ type semiconductors, for example. The electrical power terminals for semiconductor detector 10 are connected with a high voltage power source 21, and the output terminals are connected with a multichannel analyzer 23 which includes an internal A/D converter, via linear amplifier 22. Multichannel analyzer 23 is in turn connected with computer 9. For the semiconductor detector 10, depending on the type used, it may be necessary to employ a cooling mechanism using, for example, liquid nitrogen.

A video camera 24 is provided immediately above movable stage 12, whereby images of the sample to be measured mounted on movable stage 12 can be obtained and displayed on sample position verification monitor 11. With this set up, it is possible to continuously monitor the spatial relationship between the center of the X-ray beam on the sample surface and the target spot to be measured, and to adjust the X-Y position of the sample so that the X-ray beam and assay spot coincide. To indicate the position of the X-ray beam, cross hairs may be displayed on sample position verification monitor 11.

Figure 5:
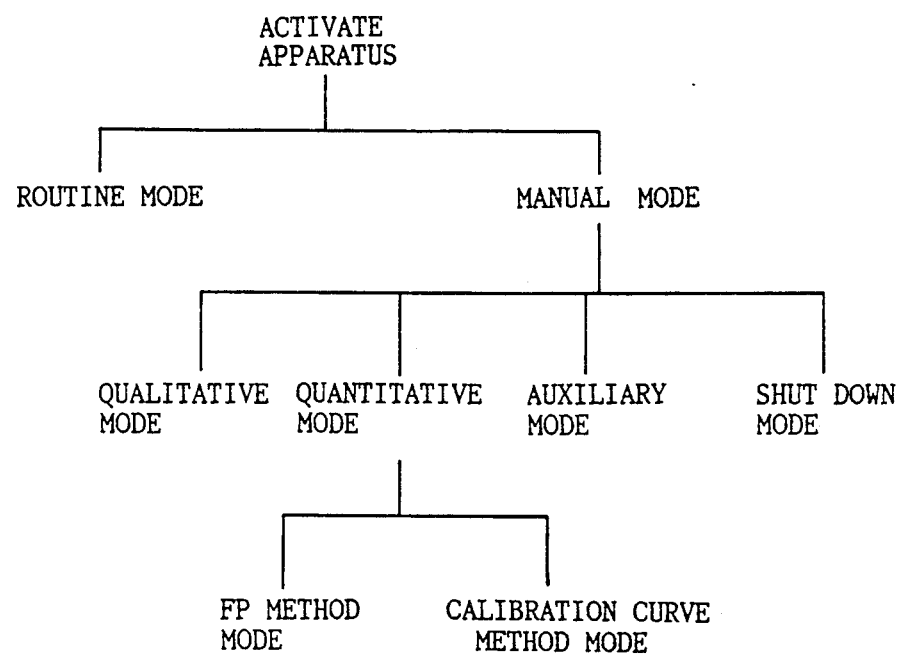
FIGS. 5 and 6 are decision trees showing the decisions involved in operating the metals assay apparatus of the present invention.
Figure 6:
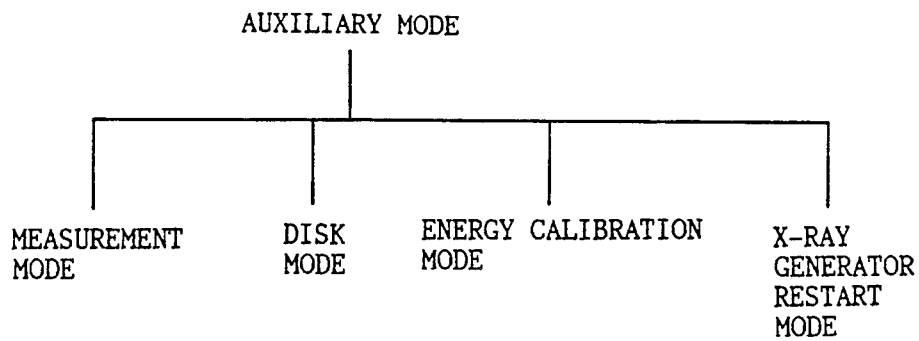

In the metals assay of the present preferred embodiment, computer 9 is programmed in such a way that number of the operating parameters can be manually selected, as will be described below and as is shown in FIGS. 5 and 6.

After the main power for the apparatus is turned on, routine mode or manual mode can be selected by the operator. Manual mode can suitably be selected for unspecified alloy samples or for samples including unusual elements. Additionally, manual mode can be employed to further refine the results obtained while carrying out an analysis in routine mode. When routine mode is chosen, selection of operating parameters is carried out on the basis of control programs in computer 9.

When manual mode has been selected, it is then possible to further manually chose between a qualitative mode for verification of metal species present, a quantitative mode for quantitation of metal species present, an auxiliary mode, and a shut down mode for terminating operation of the apparatus. In the case where quantitative mode has been chosen, it is then possible to the operator to choose between the previously described fundamental parametric method (hereafter referred to as FP method) and an analytical curve method for analysis of the obtained fluorescence X-ray spectra and quantitation of metal species present therefrom.

Once the auxiliary mode has been selected, it then becomes possible to select a measurement mode wherein the operator interacts with the apparatus via instructions displayed on display screen 4 thus establishing a dialogue whereby operating parameters are selected, according to which the assay is carried out. While in auxiliary mode, rather than the above described measurement mode, it is also possible to select a disk mode wherein the obtained data and results from an analysis are stored to a floppy disk, an energy calibration mode for calibrating parameters used for the FP method, and an X-ray restart mode whereby when X-ray control unit 19 has suddenly terminated X-ray generation due to activation of safety mechanisms for any reason, x-ray generation can be restarted after the conditions leading to the shut down have been remedied.

When routine mode has been selected by the operator, operating parameters for the FP method are set which were earlier determined in the above described energy calibration mode under manual control. In routine mode, continuous analysis of many samples can be carried out without loss of accuracy through control programs executed by computer 9.

Figure 7:
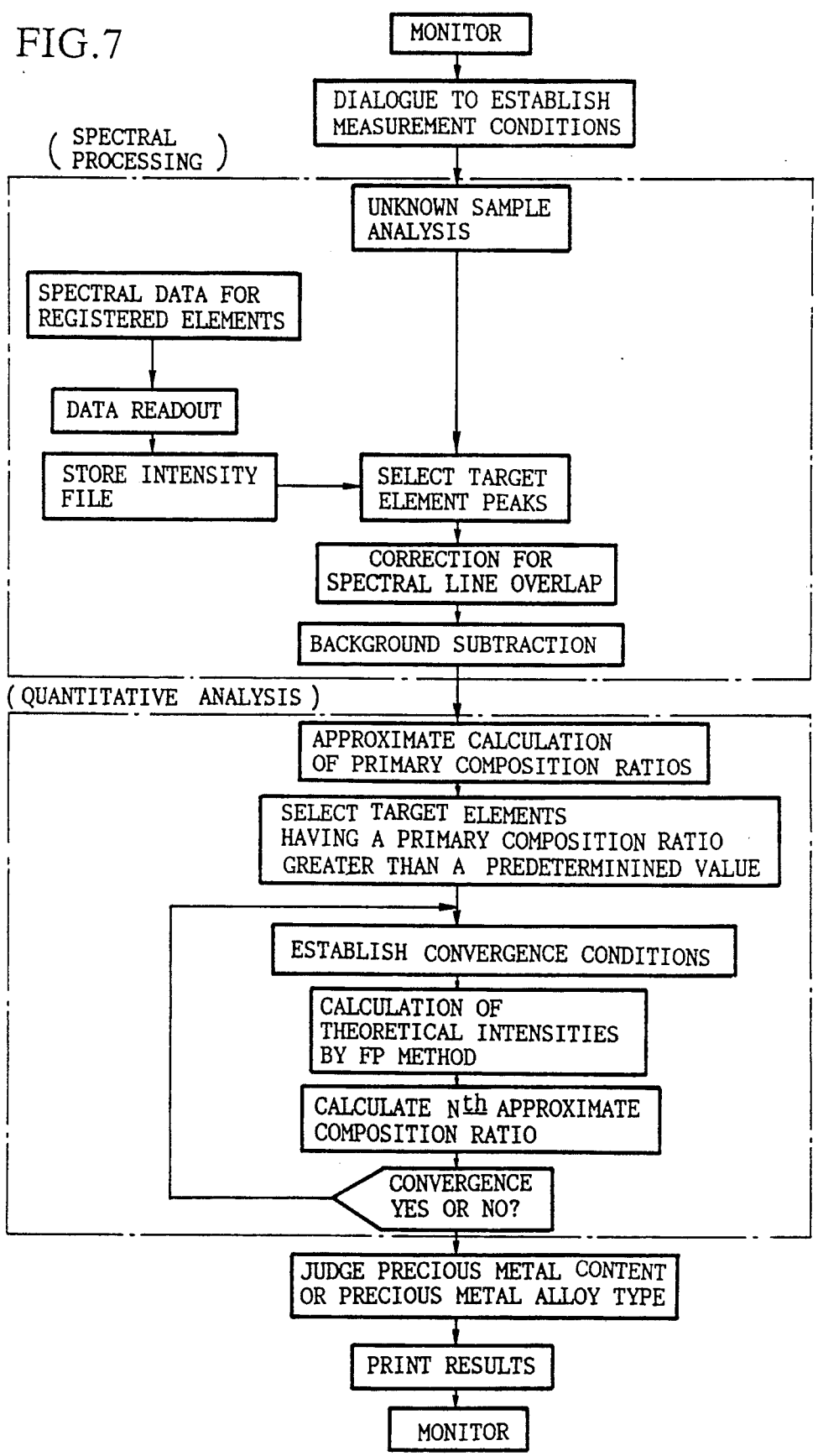
FIG. 7 is a flow chart for the fundamental parametric method.
Figure 8:
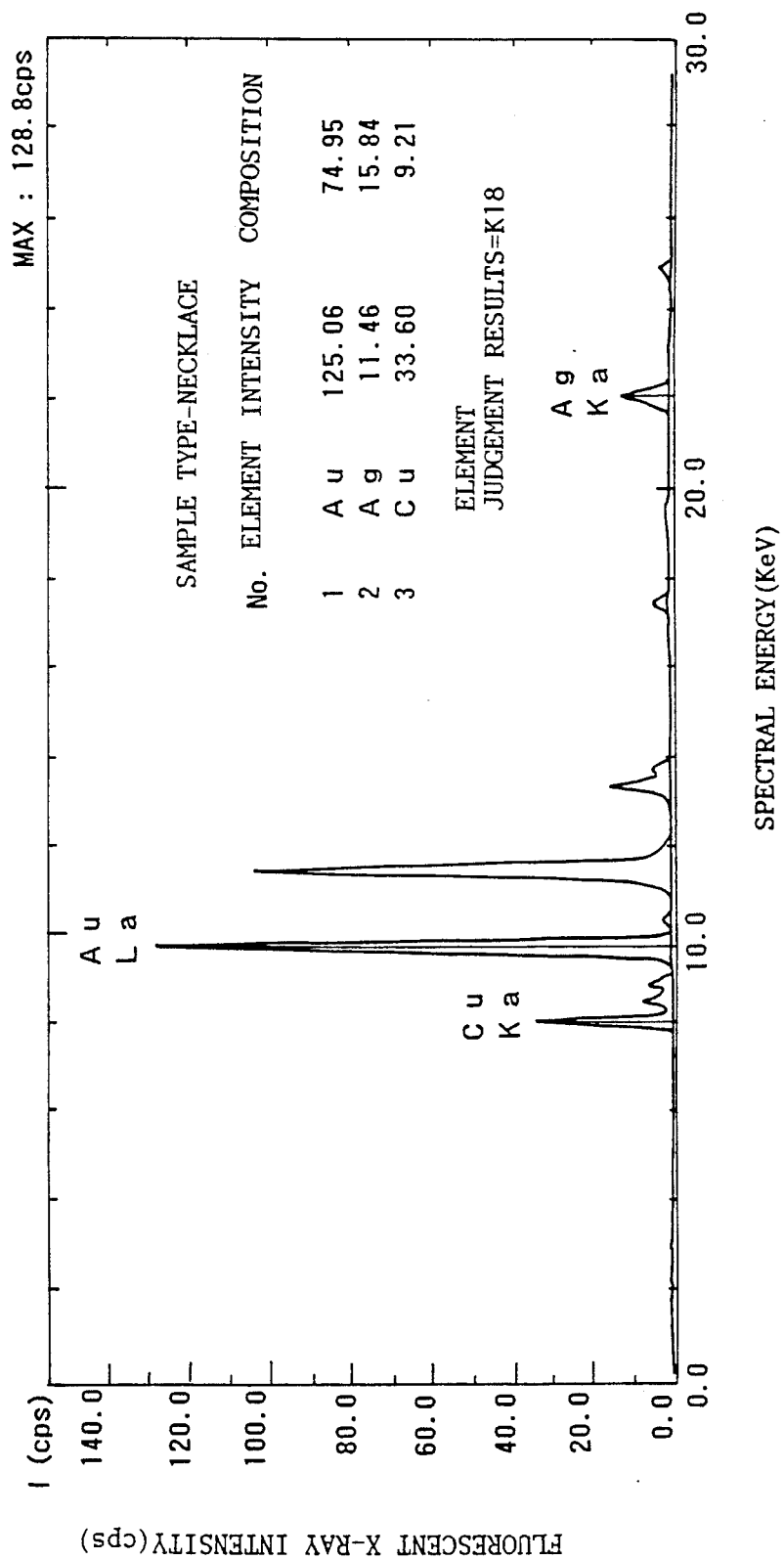
Figure 9:
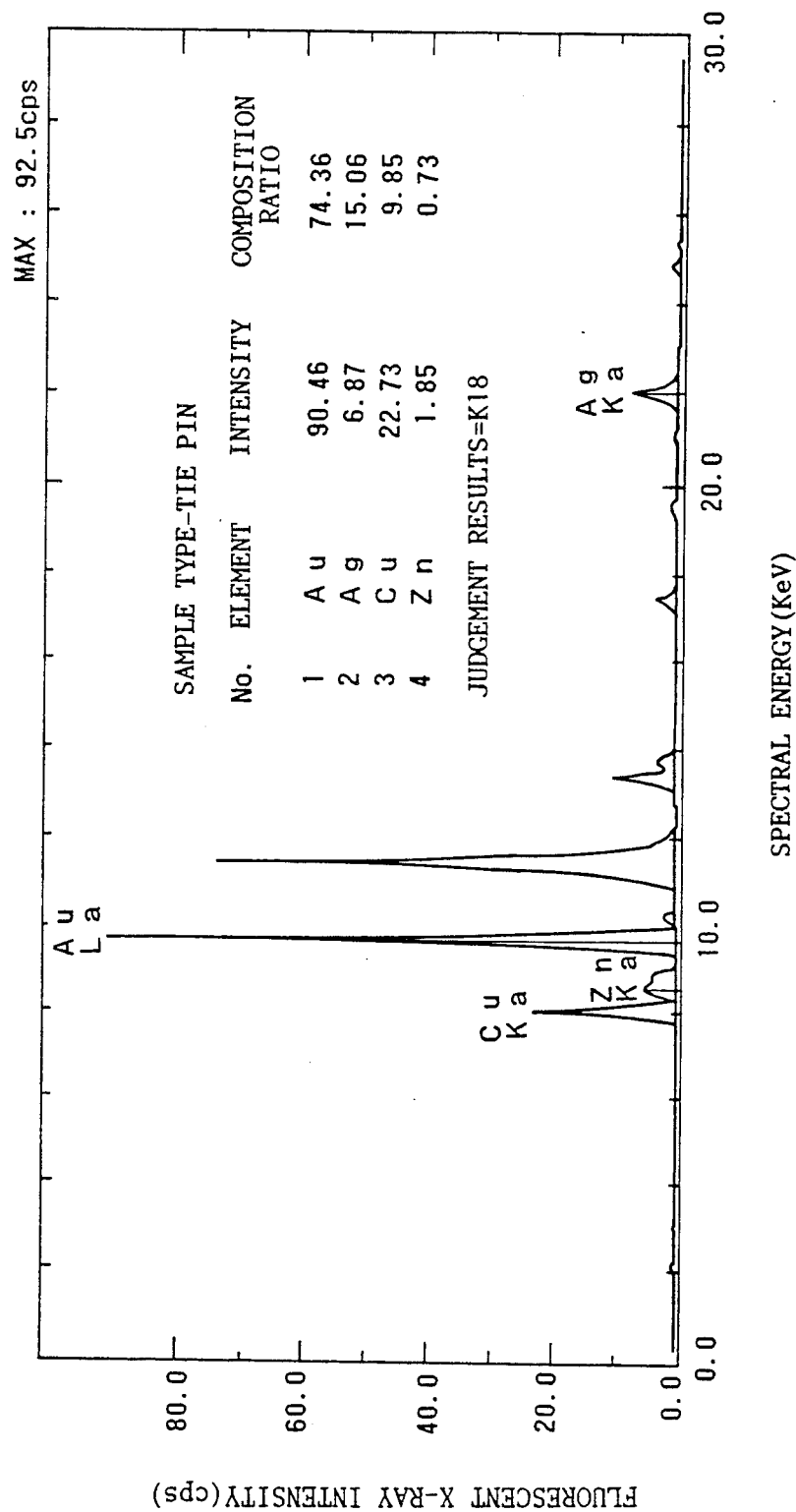
Figure 10:
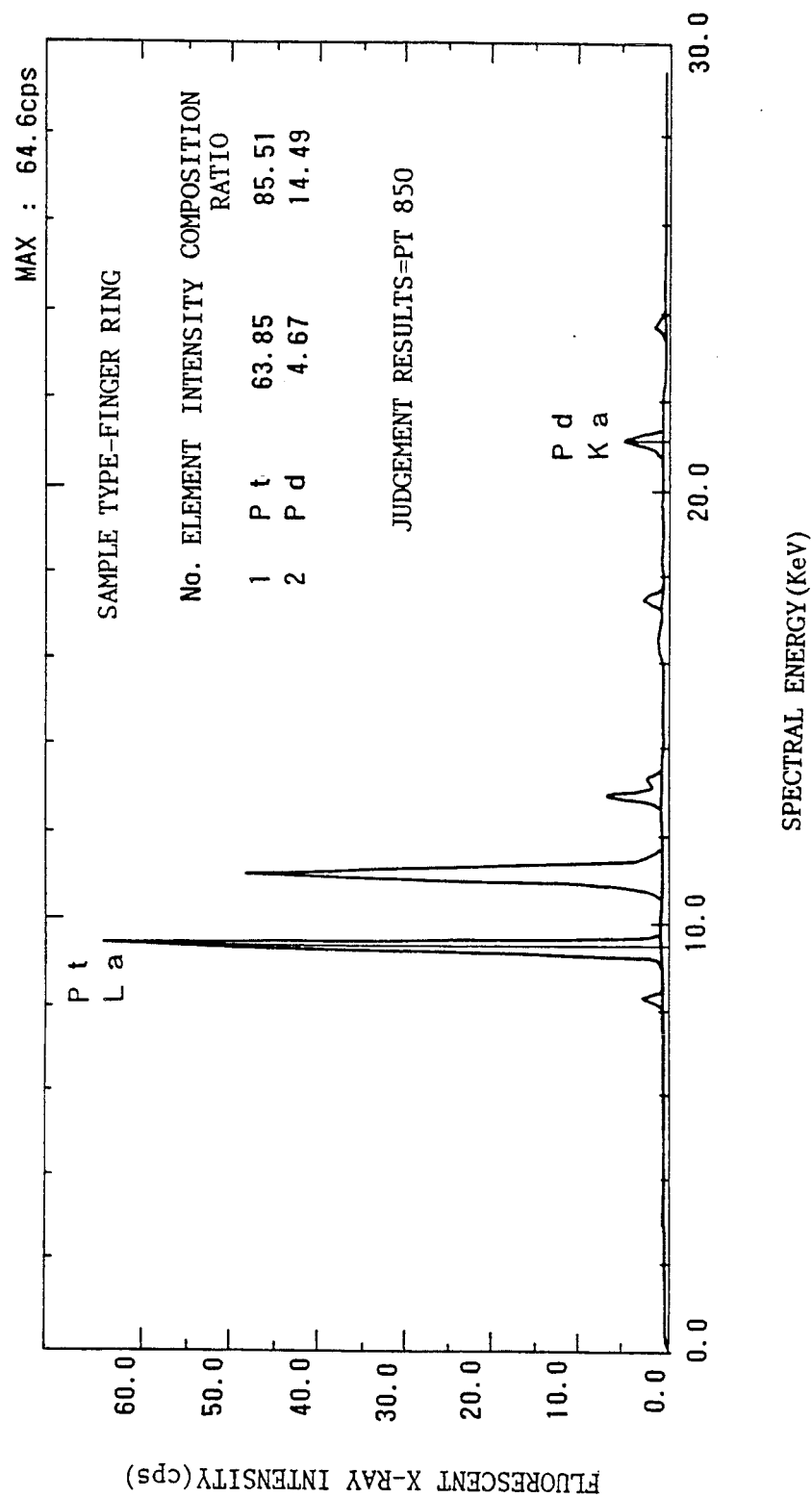
Figure 11:
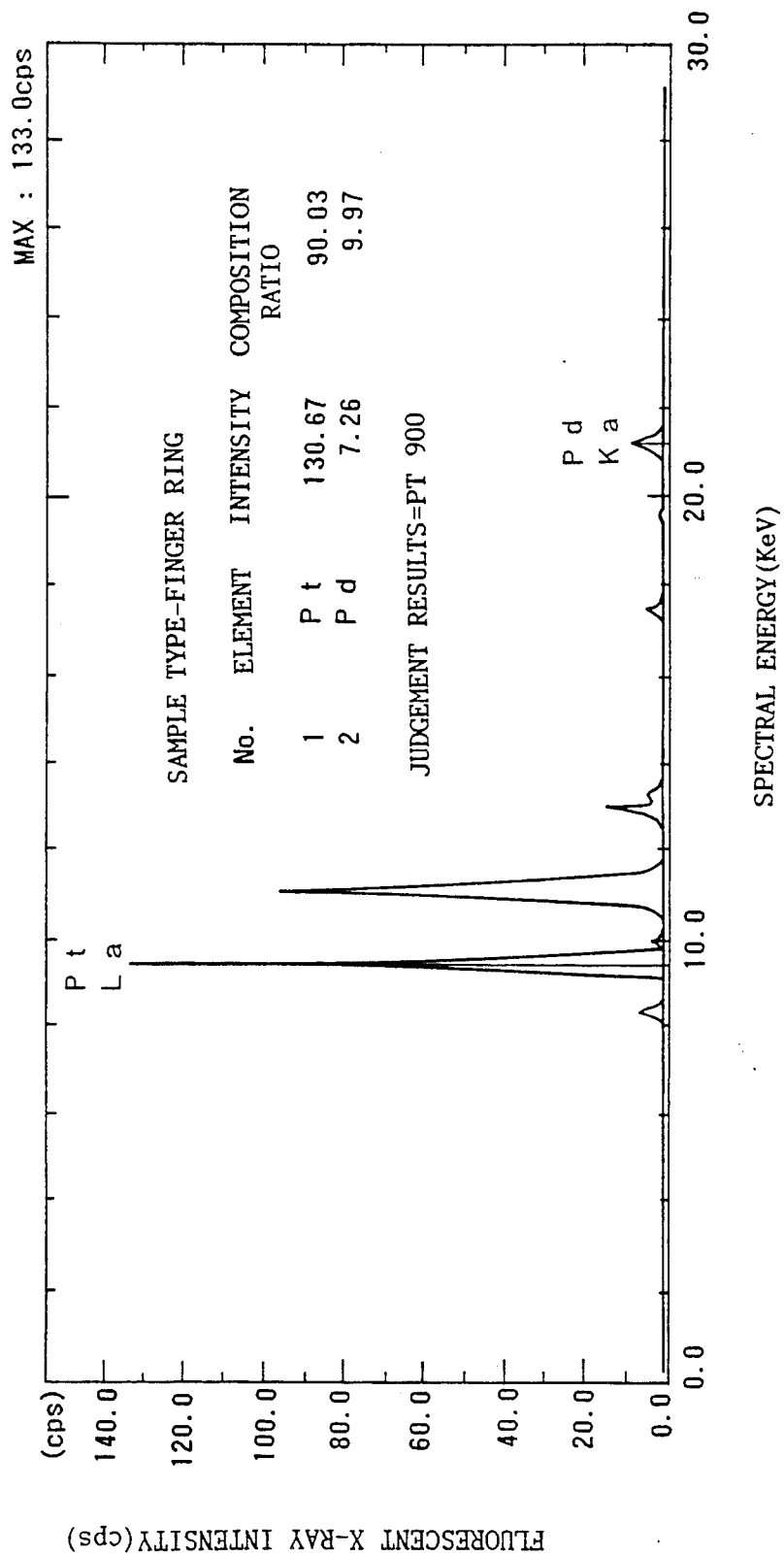
Figure 12:
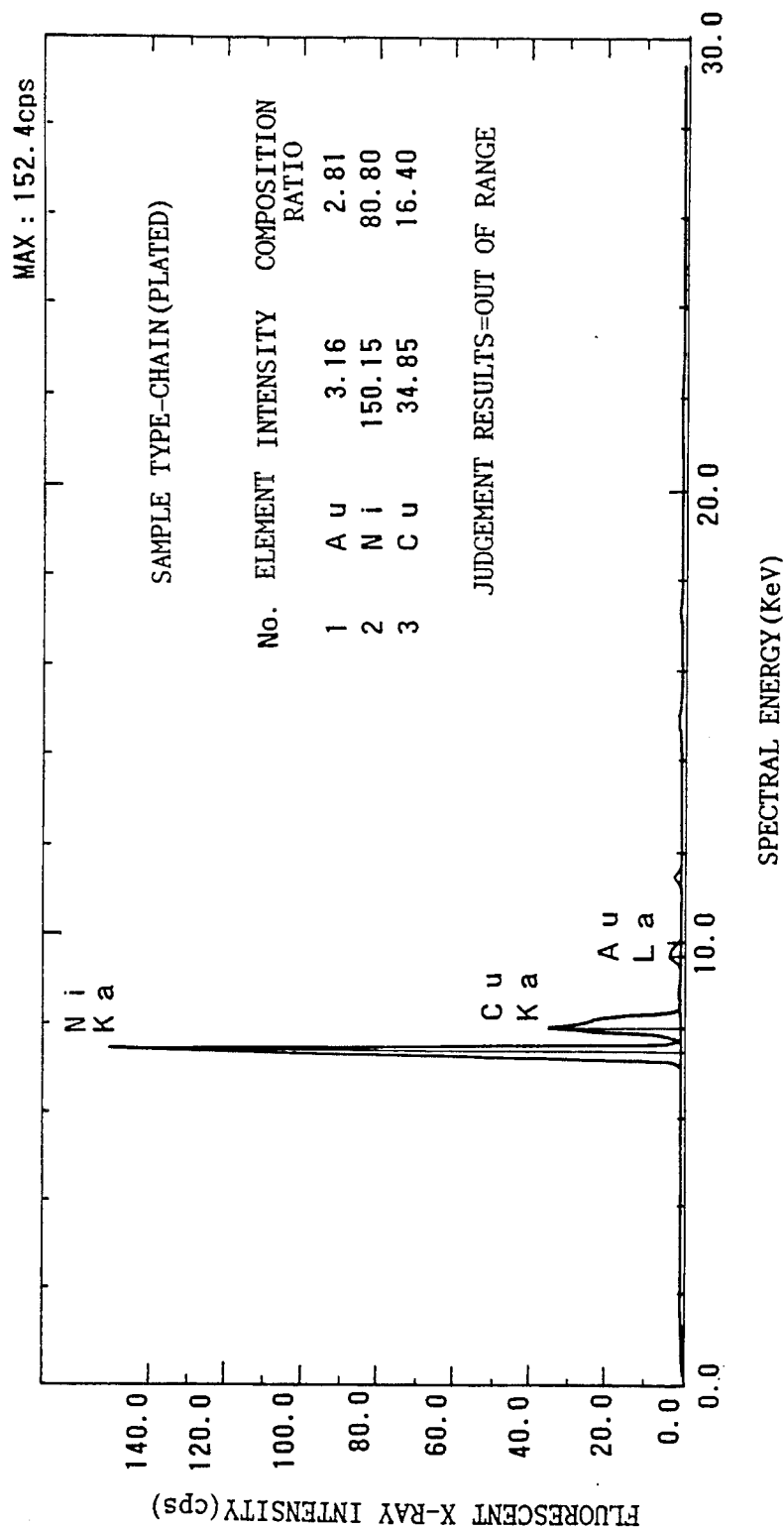
Figure 13:
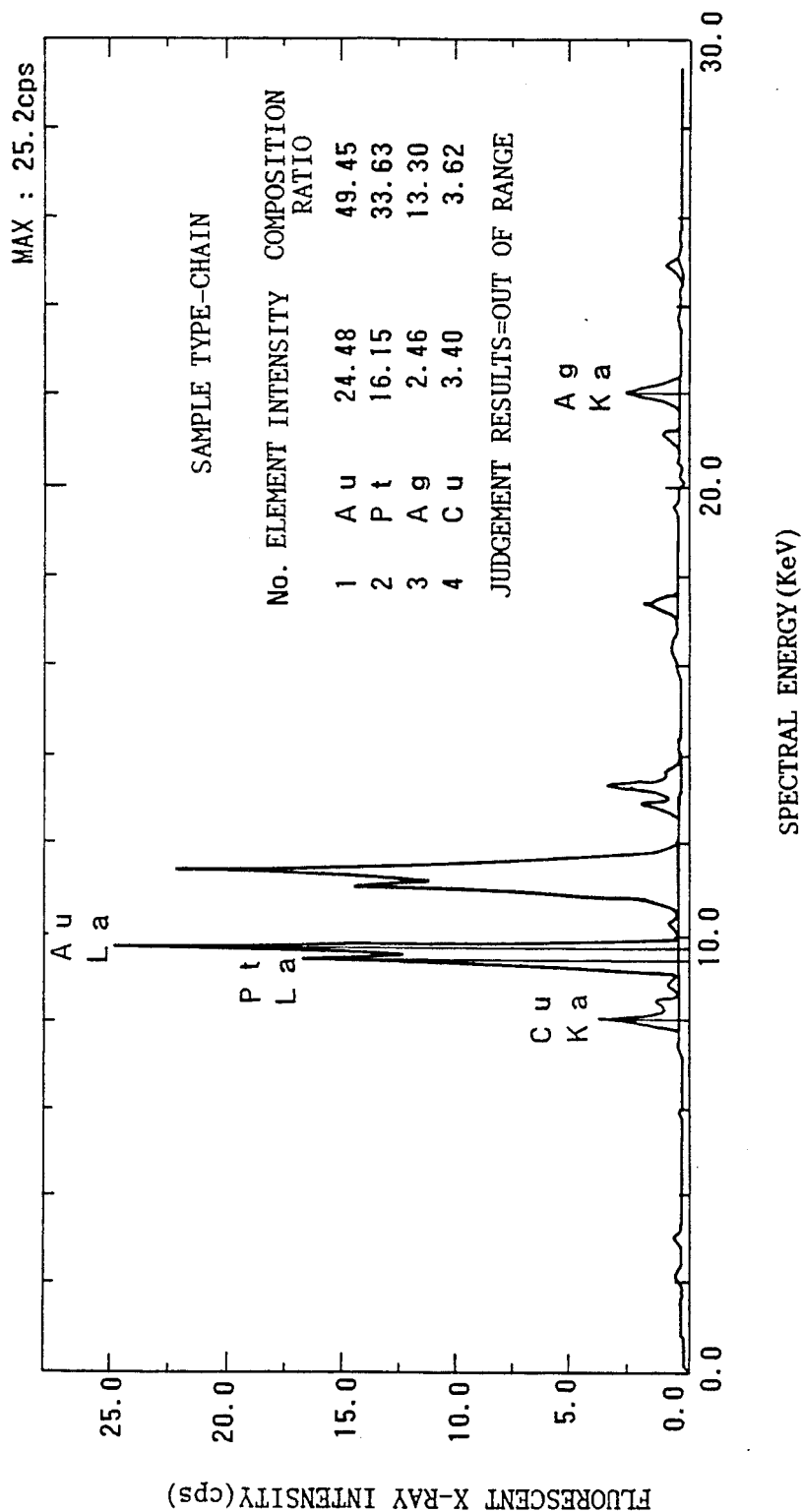
Figure 14:
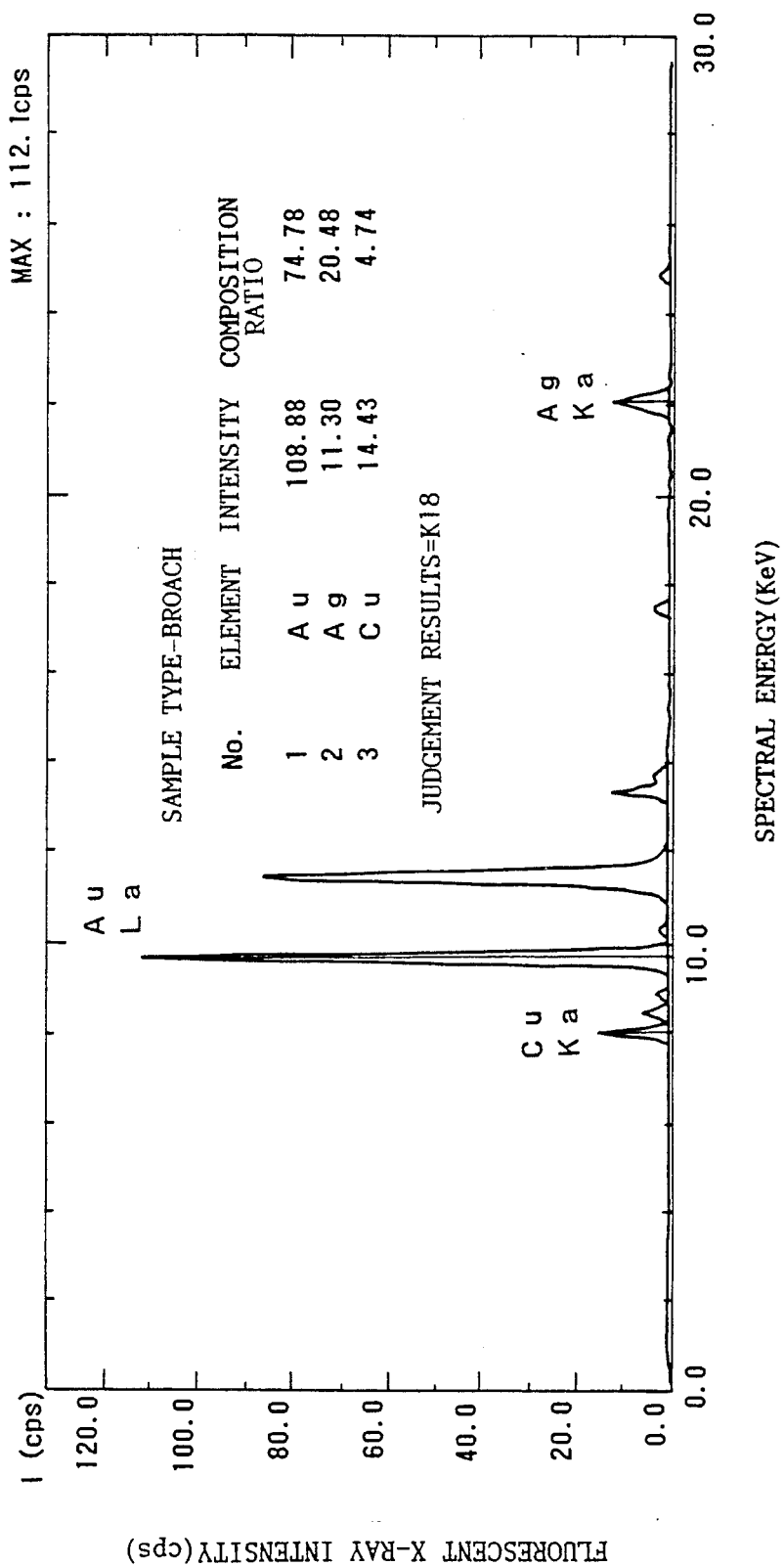

In FIG. 7, a flow chart is presented illustrating the program flow that occurs during measurement and calculations in manual mode as executed by computer 9 which will be explained below.

Peak energy value data for predetermined necessary elements (registered elements) during analysis of precious metals are registered within computer 9. These registered elements are metal species which in general are regarded as precious metals or are often included in precious metal alloys, for example one or more elements selected from the group including gold, silver, copper, nickel, zinc, platinum, palladium, rhodium, cobalt, iron, cadmium, rhenium, indium, chromium, iridium, and lead. Additionally, when unusual samples are being analyzed, other elements may be registered within computer 9.

For determining the composition of unknown samples, after spectral data is obtained, data for the registered elements is read out, and energy values for peaks in the obtained spectrum are compared with those for the registered target elements. For those peaks in the spectrum whose energy values correlate with the energy value for one of the registered elements, the correlating registered elements are selected as target elements.

Excluded from the registered elements are those elements having peaks with energy values close to the values for target elements and which can this be easily mistaken for the target elements, and furthermore which are elements which would not be expected to appear with precious metals. In this way, mistaken metal species identification can be eliminated, even when shifts occur in the peaks of the obtained spectrum.

For example, Pt—L$\alpha_1$ (9.443 keV) is close to Ga-K$\alpha$ (9.243 keV), (9.714 keV) is close to Ge—K$\alpha$ (9.876 keV), and Ag—L$\alpha_1$ (2.984 keV) is close to Ar—K$\alpha$ (2.957 keV), however, neither gallium, nor germanium, nor argon would be expected or are sought after in a precious metal alloy and are thus excluded from the registered elements. Thus, gold, silver and platinum can more reliably be identified and quantified, even when shifts in their corresponding peaks occur.

After specific registered elements have been selected as target elements, the intensities of peaks in the obtained spectrum corresponding to target elements are calculated, after which the FP method is applied to these calculated intensities to thereby determine quantitative data.

Here, a brief explanation of the FP method will be given. First of all, the calculated intensities of peaks in the obtained fluorescence X-ray spectrum are compared with intensities of the same peaks taken from corresponding fluorescence X-ray spectra previously obtained from standard pure metal samples of each registered element, on which basis, a primary composition ratio for each element is calculated. Next, from the calculated primary composition ratios, a predicted theoretical peak intensity value for each element is determined based on consideration of primary X-ray atomic absorption effects and enhancement effects. Then, for each element, the predicted theoretical peak intensity value is compared with the actually calculated value from the obtained fluorescence X-ray spectrum of the unknown sample. Iterative calculations are then carried out until the differences between the calculated values and the measured values for the peak intensities approach zero, and on the basis of these calculations, the final composition ratios are determined.

Actual calculations employed when the FP method is to be applied can generally be classified into two procedures:

1. A spectrum processing procedure in which background noise is subtracted from the obtained fluorescence X-ray spectrum, thereby determining true signal intensities.

2. A quantitation procedure in which approximate values for the primary composition ratios are determined, after which the FP method is applied to the primary approximate composition ratios to thereby obtain quantitative values for each target element.

The FP method calculations in the above described second procedure ar carried out as follows:

I. Calculation of primary approximate composition ratios

For element i, the primary approximate composition ratio $C_i^1$ is given by Equ. 1 below, where $X_i$ is the actually calculated intensity of the peak corresponding to element i in the obtained fluorescence X-ray spectrum of the alloy sample and $Y_i$ is the intensity of the same peak from a fluorescence X-ray spectrum of the pure element i.

$$C_i^1 = X_i/Y_i \qquad \text{Equ. 1}$$

It can be seen that Yi thus corresponds to the sensitivity of the apparatus.

II. Establishment of convergence conditions

When M different elemental species exist in a sample, the respective primary approximate composition ratios for each of the elements as obtained by Equ. 1 above are expressed by a series as follows:

$$C_1^1, C_2^1 C_3^1, \ldots \ldots C_m^1.$$

It follows that the sum of each primary approximate composition ratio for a given sample should be equal to one, thus yielding the following relationship:

$$\sum_{i=1}^{m} C_i^n = 1.$$

Assuming the above conditions, the secondary composition ratio $C_i^2$ for each element i is determined, using the general relation shown in Equ. 2 below for the nth order composition ratio for element i.

$$C_i^n = \frac{C_i^{n-1}}{\sum_{i=1}^{m} C_i^{n-1}} \qquad \text{Equ. 2}$$

III. Calculation of theoretical peak intensities by application of the fundamental parametric method Substituting each secondary composition ratio $C_i^2$ obtained by Equ. 2 above into an equation for inferring theoretical peak intensities using fundamental parameters, theoretical peak intensities are determined, that is, the intensities of the peaks that would be expected based on theoretical considerations. These theoretical intensities thus calculated are then compared with the corresponding actual measured peak intensities from the obtained fluorescence X-ray spectrum of the metal sample, after which tertiary approximate composition ratios $C_i^3$ are obtained.

The above described process is iterated, thus generating respective nth order approximate composition ratios $C_i^n$ for each iteration until the relationship shown in Equ. 3 below is satisfied.

$$(C_i^n - C_i^{n-1})/C_i^n << 10^{-3} \qquad \text{Equ. 3}$$

When the conditions of Equ. 3 above have been satisfied, minimum convergence conditions are judged to have been satisfied. Until the convergence conditions of Equ. 3 are satisfied, the iterative determination of $C_i^n$ for each element i is repeated. The value of $C_i^n$ for the $n^{th}$ iteration when Equ. 3 is satisfied is used as the final composition ratio Wi for element i.

In the present preferred embodiment, in the calculation process according to the above described fundamental parametric (FP) method, a supplemental routine is added as is shown in FIG. 7. Thus, in this routine, when the primary composition ratios for the target elements are calculated from the intensities of the peaks from the spectrum of the sample, a judgement is made as to whether the calculated composition ratio has reached a certain predetermined value or not, for example 1% by weight. In this case, subsequent fundamental parametric method calculations are carried out only for those target elements that have reached the predetermined minimum primary composition ratio, thereby considerably improving processing speed and efficiency.

In conventional equipment for carrying out fluorescence X-ray analysis, determinations are carried out for all measurable elements. However, in the case of the method and apparatus of the present invention, determinations for elements present in trace amounts that are not particularly sought after are automatically eliminated In this way, overly complex FP method processing can be can be limited, and determination of the composition ratios for the sought after elements can be rapidly achieved.

Moreover, in the present preferred embodiment, as is shown in FIG. 7, as the composition ratios for target elements are determined for a sample article, the determined composition ratios can be compared with predetermined composition ratios for particular precious metal alloys stored in computer 9, whereby a rapid identification of the type of alloy can be rapidly carried out. With this type of alloy identification process, it is acceptable to limit the the specific metal elements assayed and quantitated to those precious metal elements that are specifically sought after, for example gold, platinum, silver, etc.. As an example, the following grading of gold, platinum and alloys thereof can be achieved with the method and apparatus of the present invention:

| | |
|---|---|
| Au: | 57.33–58.83 Wt. % → K14 |
| | 74.00–75.50 Wt. % → K18 |
| | 90.67–92.17 Wt. % → K22 |
| Pt: | 84.00–85.50 Wt. % → Pt850 |
| | 89.00–90.50 Wt. % → Pt900 |

For any sample judged not to fall within one of the above standards, the sample is then judged as [outside standard range]. When this type of determination is carried out, the calculated composition ratio for each target element, as well as the above grading information is listed on display screen 4 and a printout of the same is produced by printer 8. Additionally, the data can be stored on a floppy disk on floppy disk drive 17 when disk mode has been selected.

When the apparatus of the present invention is to be used for metals analysis for sample materials other than precious metals and their alloys, by registering suitable data for the type of metals and alloys sought after, a grading similar to that for precious metals and precious metal alloys as shown above can be accomplished.

In the following section, method of use of the apparatus of the present invention will be described. Before use, calibration of the apparatus is required, however, calibration will be described in a later section.

In the case of unknown samples, manual and measurement mode are selected. The sample is then mounted above movable stage 12 with the surface to be assayed facing up, using an appropriate mounting jig for the shape of the sample to be assayed. With difficult to measure samples having a complicated surface with bends, indentations, protuberances and the like, strong scattering of the generated fluorescence X-rays is likely to occur, thereby increasing background in the obtained fluorescence X-ray spectrum. For this reason, with such samples, the spot to be assayed should be to the extent possible selected from an area on the surface of the sample which is flat and level.

After the sample has been mounted and aligned on movable stage 12, a collimator element having a suitably sized aperture is selected through the operation of the collimator selector mechanism of collimator 20. As described previously, for samples having a complicated surface, it is desirable to select a collimator element having a small aperture, for example, a diameter of 0.1 mm.

Next, while observing a magnified image of the upper surface of the sample on the display screen of position verification monitor 11, the positioning of the sample is adjusted by moving the X-Y position of movable stage 12 using keyboard 7 and/or mouse 6, thereby aligning the chosen area on the sample to be assayed with cross hairs indicating the spot on the sample to be exposed to X-rays. Then, movable stage drive mechanism 13 is activated and through its operation as guided by Z-axis position sensor 14, movable stage 12 moves upward from its lowermost standby position, whereby the spot on the upper surface of the sample which is to be measured is automatically brought into a predetermined position along the Z-axis in relationship to semiconductor detector 10.

The sample having been thus aligned and positioned, X-rays are directed from X-ray head 18 to the spot to be assayed, forming a 45° angle with the horizontal plane. At the same time, the generated fluorescence X-rays at the exposed spot are sampled using semiconductor detector 10 over a fixed time interval, whereby a fluorescence X-ray spectrum of the assay spot is obtained. Generally, to the extent that the aperture of the selected collimator is small, the fixed sampling time interval is long. To improve the accuracy of the obtained spectrum, the counting loss ratio for semiconductor detector 10 is determined, and on this basis, the current and voltage of the electrical power supplied to the X-ray tube within X-ray head 18 is controlled so that the counting loss ratio is no greater than 15%.

After the fluorescence X-ray spectrum has been obtained, the FP spectral analysis method mode is selected, and as has been previously described, based on a program within computer 9, elements corresponding to registered elements are selected by determining which peaks in the obtained spectrum have energy values which correspond to the energy values for peaks for registered elements previously stored in computer 9. Additionally, a correction for spectral line overlap is carried out for the peaks recognized as corresponding to registered elements, and background is subtracted from the obtained spectrum.

Next, primary composition ratios for each element identified in the preceding step are determined by comparing the peak intensities of the identified peaks, with data corresponding to the intensities of peaks for the same elements in previously obtained calibration spectra of pure samples of each of the registered elements. Those identified elements for which the calculated primary composition ratios exceed a certain predetermined value are then chosen as target elements, after which the composition ratio of each target element is determined through application of the FP method. Afterwards, based on the determined composition ratios of the target elements, judgment is made as to the type of precious metal or precious metal alloy, after which the calculated composition ratios as well as the judgment results for type of precious metal alloy are output. In cases where it is desirable to make determinations at other points on the sample surface, the position of movable stage 12 is adjusted and the entire above described process is repeated.

As mentioned earlier, energy calibration as well as calibration of parameters used in the FP method are necessary before the first use of the apparatus of the present invention. Additionally, periodic recalibration and calibration when measurement conditions have been changed considerably are recommended.

For energy calibration, energy calibration mode is selected and the position of movable stage 12 is adjusted so that the previously described energy calibration reference sample provided at one end of movable stage 12 is brought into assay position. The energy calibration reference sample is made from a material having a known composition in which the peak energy value for each component is known, for example, an alloy of gold, silver, and copper, whereby determined peak energies in an obtained calibration spectrum can be verified and corrected as necessary. Additionally, by using an energy calibration reference sample for which the composition ratio of each component is known, by reference to the determined peak intensities in an obtained calibration spectrum, the various parameters employed in the FP method can be calibrated as necessary.

While the FP method has primarily been discussed for determination of composition ratios of component metal elements, it is also possible to use a calibration curve method. However, if the calibration curve method is to be used for a wide variety of sample materials, it is necessary to have a great number of precious metal alloy reference samples extending across the range of samples that are expected to be assayed in order to prepare the calibration curves. Accordingly, costs are increased considerably. While the FP method can be used to determine the composition ratios for metal samples containing elements ranging from sodium to uranium, the FP calculations tend to be quite complicated and time consuming, particularly with complex samples. Attempts to remedy this situation by increasing the processing power of the computational circuits inevitably results in a considerable cost increase. For this reason, as has been described previously, in one method provided by the present invention, only those elements that are expected and sought after are selected as target elements, whereby processing time can be considerably compressed.

In the case when a large number of samples are to be assayed for which the component elements to be appraised are known, after calibration of the apparatus has been carried out in the manual mode using standard samples (standardization), the routine mode can be selected. In this way, multiple assays can be carried out using the FP parameter values determined during calibration in the manual mode, and the assays can be carried out nearly automatically except for sample mounting and positioning, whereby the required manual labor as well as time can be considerably reduced.

In actual use of the method and apparatus of the present invention, the following benefits can be obtained:

1. Because the Fluorescence X-ray spectrometry method is nondestructive, an assay can be carried out without diminishing the value or salability of the sample. Furthermore, by an operator with ordinary skills and experience, a sample can easily and reliably be simultaneously assayed for a plurality of metal elements in a relatively short time period. Moreover, other than sample mounting and positioning, multiple assays can be carried out automatically, thus considerably reducing manual labor and time consumption. Thus, the method and apparatus of the present invention is quite applicable to the business sites for dealers in jewelry, precious metals, coins and the like.

2. Both qualitative and quantitative analysis of unknown samples is possible.

3. Because apertures from 0.1 to 5 mm are selectable for collimator 20, samples of many sizes and configurations can be assayed. Thus, samples having at least one surface that is flat and relatively broad can quickly and accurately be assayed using an apertures of 5 mm for collimator 20, while using an apertures of 0.1 mm, small samples having complex surfaces can be reliably assayed. Additionally, composite samples comprised of more than one kind of metals or alloys can be assayed at multiple sites and the size of the area to be assayed can be selected by the operator to suit the sample and other requirements. Furthermore, by assaying the sample at multiple locations, the consistency of the composition of the sample surface can be verified. Moreover, because the assay is carried out on a surface layer on the order of 30 μm in depth, plated items can be distinguished.

4. While viewing a magnified image of the surface of the sample to be assayed using sample position verification monitor 11, the X-Y position of movable stage 12 can be accurately adjusted using mouse 6 to select the desired spot to be assayed. After the X-Y position has be selected, then the sample is automatically brought into the optimum position along the Z-axis through the action of Z-axis position sensor 14. Thus, the sample can rapidly and reliably be brought into the optimum position for assay.

5. Since the entire apparatus is contained in or on a unitary chassis, floor space requirements can be reduced allowing the apparatus to be used at relatively small business locations.

6. Because FP calculations are directed only towards elements that are expected and/or sought after, time requirements can be considerably reduced. Thus, multiple samples can be assayed in a relatively short period of time.

7. Through use of the fundamental parametric (FP) method, analysis for multiple metal elements can be carried out simultaneously, even for unknown samples. Furthermore, there is no need for a great number of standard samples as is the case when the calibration curve method is employed.

8. By selecting only those metal elements whose primary composition ratios are greater than a predetermined value for target elements, calculations for contaminants and other elements present in trace amounts are eliminated, thus reducing the time and complexity of FP method calculations, as well as the processing power requirements for computer 9.

9. By comparing the energy values for peaks in the obtained spectrum with energy values for the registered elements previously stored in computer 9, the presence or absence of registered elements in a sample can rapidly be verified. Further, by limiting the registered elements to only those elements that are sought after, misidentification of metal elements can be eliminated, even when shifts occur in the obtained spectra.

10. By comparing determined composition ratios with values stored in computer 9 for standard precious metal alloys, rapid and automatic grading of samples can be achieved. Furthermore, much more reliable grading is possible than with conventional methods such as the touchstone method and the grading is accomplished without marring or otherwise adversely affecting the sample.

The description of the preferred embodiments of the method and apparatus of the present invention in the preceding sections has largely centered on analysis of precious metal samples, however, the invention is in no way so limited. In addition to precious metal materials, examples of other applications of the precious invention include analysis of superconducting materials, ceramics, and all other types of metal and alloy materials. Details of the implementation of the present invention can of course be varied to suite the type of materials to be assayed and the conditions under which assays are to be carried out.

In the following, the results of actual application of the method and apparatus of the present invention will be presented in the fore of experimental examples.

EXPERIMENTAL EXAMPLE 1

Using the apparatus shown in FIGS. 1 through 4, the composition of metal ingots was assayed and the obtained results were compared with results obtained through a conventional chemical analysis. For samples, commercial gold ingots ranging from K14 to K18 were used and analysis was carried out under the conditions shown directly below. The results of the above analysis are shown in Table 1 below.

| X-ray tube voltage: | 50 kV |
| X-ray tube current: | 5 mA |
| X-ray tube target: | molybdenum |
| collimator aperture: | 1.0 mm |
| length of measurement: | 100 sec. |

TABLE 1

| | Sample | K14 | K16 | K18 | K18 (white) | K18 (yellow) | K18 (pink) |
|---|---|---|---|---|---|---|---|
| Au | Present Invention | 57.7% | 66.2% | 75.6% | 75.7% | 74.8% | 74.6% |
| | Chemical Method | 58.3% | 66.7% | 75.0% | 75.2% | 75.2% | 75.2% |
| Ag | Present Invention | 42.3% | 33.8% | 22.4% | 4.8% | 19.9% | 5.4% |
| | Chemical Method | 41.2% | 33.3% | 25.0% | 4.9% | 20.0% | 5.0% |
| Cu | Present Invention | — | — | — | — | 4.9% | 19.9% |
| | Chemical Method | — | — | — | — | 5.3% | 20.0% |
| Pd | Present Invention | — | — | — | 19.5% | — | — |
| | Chemical Method | — | — | — | 20.0% | — | — |

As can be seen in Table 1 above, the results obtained using the method and apparatus of the present invention are quite close to those obtained through a conventional chemical analysis. Thus, through application of the present invention, reliable and rapid results are attainable, and additionally, with no damage to the sample as with a chemical analysis method.

EXPERIMENTAL EXAMPLE 2

As a sample, a tie pin was fabricated by applying a plating of silver over a nickel base, furthermore applying a gold plating, after which the sample was assayed using the apparatus and method of the present invention under identical conditions as for the Experimental Example 1. It was determined that the X-rays penetrated the sample to a depth of on the order of 30 μm. The results obtained are as follows:

| | |
|---|---|
| Gold: | 6.8% |
| Silver: | 34.4% |
| Nickel: | 57.3% |

Thus, it can be seen that the fact that the sample was plated could be distinguished.

EXPERIMENTAL EXAMPLE 3

Using a variety of fashion accessories of unknown composition as samples, each article was assayed using the apparatus and method of the present invention under identical conditions as for the Experimental Example 1. The obtained results including judgement of metal type are shown in FIGS. 8 through 16.

What is claimed is:

1. A metals assay method comprising the steps of:
   a) preparing a sample;
   b) establishing a group of registered elements and storing standard spectral data for the registered elements;
   c) exposing said sample to an X-ray beam, whereby fluorescence X-ray radiation is generated;
   d) obtaining experimental spectral data by sampling said fluorescence X-ray radiation;
   e) identifying which of said registered elements are significantly present in said sample by comparing said experimental spectral data with said standard spectral data;
   f) determining an intensity of a corresponding peak for each identified element and comparing each determined intensity with respective standard spectral data for each of said identified elements, thereby obtaining preliminary quantitative data for each of said identified elements; and
   (g) further analyzing said preliminary quantitative data whereby more precise quantitative data is obtained for said identified elements;
   wherein said step of further analyzing said preliminary quantitative data consists of submitting said preliminary quantitative data to fundamental parametric analysis.

2. A metals assay method in accordance with claim 1 in which after obtaining said experimental spectral data, said experimental spectral data is analyzed to determine the energy value that corresponds to each significant peak in said experimental spectral data, after which, in said step of identifying which of said registered elements are significantly present, said comparing said experimental spectral data with said standard spectral data is carried out by comparing the determined energy values with the standard energy values for said registered elements.

3. A metals assay method according to claim 1 which further comprises the step of:
   h) based on said preliminary quantitative data, determining which of said identified elements are present above a predetermined amount, thereby selecting target elements, and performing step (g) using only said target elements.

4. A metals assay method in accordance with claim 1 wherein said registered elements are selected from the group including gold, silver, copper, nickel, zinc, platinum, palladium, rhodium, cobalt, iron, cadmium, rhenium, indium, chromium, iridium, and lead.

5. A metals assay method in accordance with claim 1 wherein said more precise quantitative data is compared with predetermined composition ratios, thereby determining the alloy type of said sample.

6. A metals assay method comprising the steps of:
   a) aligning a sample so that a portion of a surface of said sample constituting an X-ray exposure spot substantially coincides with a path of an X-ray beam which will be generated, said exposure spot substantially coinciding with a point on the surface of said sample where it is intended to carry out said metals assay;
   b) exposing said exposure spot to an X-ray beam of 0.1 to 5 mm in diameter, whereby fluorescence X-ray radiation is generated at said exposure spot;
   c) obtaining experimental spectral data by sampling said fluorescence X-ray radiation that is generated;
   d) determining the energy value corresponding to each peak in said experimental spectral data;
   e) comparing said energy values with predetermined energy values for registered elements, thereby determining if said peaks in said experimental spectral data correspond to registered elements, whereby elements present in said sample that are included among said registered elements are identified;
   f) determining the intensity of said peaks in said experimental spectral data that correspond to registered elements, thereby determining a primary composition ratio for each registered element that is determined to be present in said sample;
   g) selecting those elements for which the determined primary composition ratio is greater than a predetermined value, thereby selecting target elements; and
   h) carrying out a fundamental parametric analysis on the primary composition ratios corresponding to said target elements, thereby determining quantitative data for said sample.

7. A metals assay method in accordance with claim 6 above wherein said registered elements are selected from the group including gold, silver, copper, nickel, zinc, platinum, palladium, rhodium, cobalt, iron, cadmium, rhenium, indium, chromium, iridium, and lead.

8. A metals assay method in accordance with claim 6 above wherein said quantitative data is compared with predetermined composition ratios thereby determining the alloy type of said sample.

9. A fluorescence X-ray spectrometry metals assay apparatus for assaying the metal content of a sample at an exposure spot located on a surface of said sample, said exposure spot being an area at which it is desired to carry out said assay and at which an X-ray beam will be directed during said assay, said sample defining an X-Y plane which is substantially parallel to the surface of said sample at said exposure spot, and a Z-axis which is perpendicular to said X-Y plane, said fluorescence X-ray spectrometry metals assay apparatus including:
   a) a movable stage on which a sample is capable of being temporarily mounted, the position of said movable stage being adjustable in three dimensions;
   g) an X-Y axis drive mechanism whereby the position of said movable stage can be adjusted in said X-Y plane;

c) a Z-axis drive mechanism whereby the position of said movable stage can be adjusted along said z-axis;

d) a television camera and monitor, said television camera positioned so as to obtain an image of at least a portion of a surface of said sample, said of at least a portion of said surface including said exposure spot, said captured image being displayed on said monitor so that the relationship of said exposure spot and an X-ray beam that will be generated is displayed, whereby said exposure spot can be made to coincide with said X-ray beam that will be generated;

e) a Z-axis position sensor whereby the position of said exposure spot relative to said Z-axis can be detected, and by means of the output of said Z-axis position sensor, said Z-axis drive mechanism can be caused to automatically drive said movable stage, thereby bringing said exposure spot into an optimum position for carrying out said assay;

f) an X-ray source equipped with a collimator, whereby and X-ray beam of a diameter of from 0.1 to 5 mm can be directed at said exposure spot on said sample;

g) a solid state sensor whereby fluorescence X-ray radiation which is generated at said exposure spot when said exposure spot is exposed to said X-ray beam can be sampled; and h) a computer by which means based on the output of said solid state sensor, experimental fluorescence X-ray spectral data for said sample from said exposure spot can be obtained and compared with standard data, whereby said computer determines the energy values corresponding to each peak in said experimental fluorescence X-ray spectral data, after which said computer compares said energy values with predetermined energy values for registered elements, thereby determining if said peaks in said experimental spectral data correspond to registered elements, whereby elements present in said sample that are included among said registered elements are identified, after which said computer then determines the intensity of said peaks in said experimental spectral data that correspond to registered elements, thereby determining a primary composition ratio for each registered element that is determined to be present in said sample, after which those elements for which the determined primary composition ratio is greater than a predetermined value are selected, thereby selecting target elements, after which, said primary composition ratios corresponding to said target elements are subjected to fundamental parametric analysis, thereby determining quantitative data for said sample.

10. A metals assay method comprising the steps of:
a) preparing a sample;
b) establishing a group of registered elements and storing standard spectral data for the registered elements;
c) exposing said sample to an X-ray beam, whereby fluorescence X-ray radiation is generated;
d) obtaining experimental spectral data by sampling said fluorescence x-ray radiation;
e) identifying which of said registered elements are significantly present in said sample by comparing said experimental spectral data with said standard spectral data;
f) determining an intensity of a corresponding peak for each identified element and comparing each determined intensity with respective standard data for each of said identified elements, thereby obtaining a primary composition ratio for each of said identified elements;
g) calculating a theoretical peak intensity for each of said identified elements using said primary composition ratios;
h) comparing each of said peak intensities of said identified elements with a corresponding theoretical peak intensity, and determining respective higher order composition ratios;
i) calculating a theoretical peak intensity for each of said elements using said higher order composition ratios;
j) repeating said steps (h) and (i) until each of said respective differences between each of said peak intensities of said identified elements and a corresponding of said theoretical peak intensities calculated from said higher order composition ratios reaches a predetermined threshold, thereby obtaining a final composition ratio.

11. A metals assay method in accordance with claim 10, wherein said steps (f)–(j) comprise:
calculating said primary composition ratio for each of said identified elements i using the formula:

$$C_i^1 = X_i/Y_i$$

wherein $C_i^1$ is said primary composition ratio for said identified element i, $X_i$ is the determined intensity of a peak for said identified element i, and $Y_i$ is an intensity of said peak from a fluorescence X ray spectrum of said identified element i in pure form;

calculating nth order composition ratios for each of said identified elements i using the formula:

$$C_i^n = \frac{C_i^{n-1}}{\sum_{i=1}^{m} C_i^{n-1}}$$

wherein m is the number of said identified elements i; and determining $C_i^n$ as said final composition ratio for each of said identified elements i when:

$$(C_i^n - C_i^{n-1})/C_i^n << 10^{-3}.$$

12. A metals assay method in accordance with claim 10 wherein said final composition ratio is compared with predetermined composition ratios, thereby determining the alloy type of said sample.

* * * * *